United States Patent
Kushida (10) Patent No.: US 8,057,040 B2
(45) Date of Patent: Nov. 15, 2011

(54) OPHTHALMOLOGIC PHOTOGRAPHING APPARATUS

(75) Inventor: Akihiro Kushida, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 19 days.

(21) Appl. No.: 12/581,767

(22) Filed: Oct. 19, 2009

(65) Prior Publication Data

US 2010/0097574 A1  Apr. 22, 2010

(30) Foreign Application Priority Data

Oct. 20, 2008 (JP) ................................. 2008-269957

(51) Int. Cl.
*A61B 3/14* (2006.01)
*A61B 3/10* (2006.01)
(52) U.S. Cl. ....................................... 351/206; 351/205
(58) Field of Classification Search ........... 351/200–246
See application file for complete search history.

(56) References Cited

U.S. PATENT DOCUMENTS

| | | | | |
|---|---|---|---|---|
| 4,436,388 A * | 3/1984 | Takahashi et al. | ............ | 351/206 |
| 5,118,179 A * | 6/1992 | Sano et al. | ................... | 351/206 |
| 5,565,938 A | 10/1996 | Hanamura | ..................... | 351/206 |
| 7,735,999 B2 * | 6/2010 | Mizuochi | ...................... | 351/206 |
| 2006/0126017 A1 | 6/2006 | Mizuochi | ...................... | 351/206 |
| 2006/0280489 A1 | 12/2006 | Mizuochi | ...................... | 351/206 |
| 2009/0251665 A1 * | 10/2009 | Hara | ............................ | 351/206 |

FOREIGN PATENT DOCUMENTS

| | | |
|---|---|---|
| EP | 1752084 | 2/2007 |
| EP | 1908399 | 4/2008 |
| JP | H07-136124 A | 5/1995 |
| JP | 9-66030 A | 3/1997 |
| JP | 2003-093348 | 4/2003 |
| JP | 2004-180705 A | 7/2004 |
| JP | 2008-055010 | 3/2008 |
| JP | 04-138133 | 8/2008 |

* cited by examiner

*Primary Examiner* — Mohammed Hasan
(74) *Attorney, Agent, or Firm* — Canon U.S.A., Inc., IP Division (57) ABSTRACT

Upon detecting a selection of an examination start button, a start and completion management unit starts an examination. The control unit switches an observation state to an infrared light observation by an observation switching unit. Next, an examiner performs alignment while observing an eye to be examined, and photographs the eye to be examined with a photographing unit. The start and completion management unit determines whether the examination is completed according to a selection of an examination complete button, and repeats the alignment until it is determined that the examination is completed.

16 Claims, 12 Drawing Sheets

| INPUT MYDRIATIC INFORMATION | ☒ |

MYDRIATIC INFORMATION

INSTILLATION OF MYDRIATIC AGENT    ○ NOT INSTILLED  ● INSTILLED

TYPE OF MYDRIATIC AGENT    [ ATROPINE ▼ ]

DIAMETER OF PUPIL (mm)  [          ]

[ OK ]    [ CANCEL ]

| EXAMINATION IDENTIFIER | MYDRIASIS INFORMATION INPUT STATE | OBSERVATION STATE | OBSERVATION CONTROL STATE |
|---|---|---|---|
| EXAMINATION 1 | MYDRIATIC AGENT IS NOT INSTILLED | INFRARED LIGHT OBSERVATION | PROHIBIT SWITCHING OF OBSERVATION UNITS |
| EXAMINATION 2 | MYDRIATIC AGENT IS INSTILLED | VISIBLE LIGHT OBSERVATION | PERMIT SWITCHING OF OBSERVATION UNIT |
| EXAMINATION 3 | MYDRIATIC AGENT IS INSTILLED | INFRARED LIGHT OBSERVATION | PERMIT SWITCHING OF OBSERVATION UNIT |
| EXAMINATION 4 | NOT YET INPUT | INFRARED LIGHT OBSERVATION | PROHIBIT SWITCHING OF OBSERVATION UNIT |

INPUT MYDRIATIC INFORMATION

RIGHT EYE
- INSTILLATION OF MYDRIATIC AGENT: ○ NOT INSTILLED ● INSTILLED
- TYPE OF MYDRIATIC AGENT: ATROPINE ▼
- DIAMETER OF PUPIL (mm): [    ]

LEFT EYE
- INSTILLATION OF MYDRIATIC AGENT: ○ NOT INSTILLED ● INSTILLED
- TYPE OF MYDRIATIC AGENT: ATROPINE ▼
- DIAMETER OF PUPIL (mm): [    ]

[ OK ]  [ CANCEL ]

FIG. 11

| LEFT AND RIGHT EYES | MYDRIASIS INFORMATION INPUT STATE | OBSERVATION STATE | OBSERVATION CONTROL STATE |
|---|---|---|---|
| RIGHT EYE | MYDRIATIC AGENT IS NOT INSTILLED | INFRARED LIGHT OBSERVATION | PROHIBIT SWITCHING OF OBSERVATION UNIT |
| LEFT EYE | MYDRIATIC AGENT IS INSTILLED | VISIBLE LIGHT OBSERVATION | PERMIT SWITCHING OF OBSERVATION UNIT |

FIG. 12

OPHTHALMOLOGIC PHOTOGRAPHING APPARATUS

BACKGROUND OF THE INVENTION

1. Field of the Invention

The present invention relates to an opthalmologic photographing apparatus that enables switching between an infrared light observation and a visible light observation.

2. Description of the Related Art

Generally, an eye fundus photography for capturing an image of a fundus of an eye to be examined includes a non-mydriatic photography for capturing (photographing) an image thereof without a mydriatic agent being instilled into the eye to be examined, and a mydriatic photography for capturing an image thereof with the mydriatic agent being instilled into the eye to be examined are known. In the non-mydriatic photography, the eye fundus photographing is performed by causing the eye to be in state of natural mydriasis in a dark place, and an observation is made using infrared light in order to prevent the pupil of the eye from narrowing (i.e., to prevent miosis) during an observation.

On the other hand, in the mydriatic photography, the eye fundus photographing is performed in a state where the pupil of an eye to be examined is forcibly dilated by the mydriatic agent. In the mydriatic photography, since the miosis does not occur even if visible light is irradiated, an observation with visible light is generally performed. However, the observation may be conducted with infrared light in order to reduce burden to the eye to be examined.

Japanese Patent Application Laid-Open No. 9-66030 discusses a combined machine that can perform both the non-mydriatic photographing and the mydriatic photographing. In the combined machine, an examiner can switch the mode between the non-mydriatic photographing mode and the mydriatic photographing mode. Thereby the photographing is performed by switching the mode to the infrared light observation during the non-mydriatic photographing, and to the visible light observation during the mydriatic photographing.

Fluorescence photography in which the photographing is performed with the fluorescent agent being injected intravenously into the body of an examinee, requires an examination time of normally 10 to 30 minutes or longer. In general, during the initial stage of fluorescence in the fluorescence photography, since the amount of change of an observed image due to inflow of the fluorescent agent is large, a number of photographs need to be taken in a short time. However, during the later stage of the fluorescence in which the fluorescent agent has been circulated throughout the eye fundus, a photographing interval is taken longer since the amount of change of the observed image is small.

In the fluorescence photography, when many examinees are photographed, another examinee may be sometimes photographed during the first examinee's photographing interval during the later stage of fluorescence, in order to enhance the overall photographing efficiency.

Japanese Patent Application Laid-Open No. 2004-180705 discusses an apparatus that can concurrently implement a plurality of examinations in order to handle such cases. However, when the examination that is performed with a photographing apparatus is changed from the examination of an examinee who is undergoing a visible light observation with the mydriatic agent being instilled into the eye, to an examinee who is to undergo an infrared light observation without the mydriatic agent being instilled into the eye, an examiner may forget a mode switching from the visible light observation to the infrared light observation. Further, when the infrared light observation is performed without the mydriatic agent being instilled into the eye, an examiner may switch the mode to the visible light observation by an operational mistake.

When visible light is irradiated to an eye of an examinee who has not undergone instillation of the mydriatic agent, the pupil of the eye may be narrowed. Once the pupil of the eye to be examined is narrowed, a waiting time until the pupil is open again may be needed, and photographing efficiency may be deteriorated.

SUMMARY OF THE INVENTION

The present invention is directed to an opthalmologic photographing apparatus that can prevent visible light from being irradiated on an eye to be examined into which a mydriatic agent has not been instilled, even when an examiner forgets to switch mode from a visible light observation to an infrared light observation, and prevent operational mistake of switching to the visible light observation.

According to an aspect of the present invention, an opthalmologic photographing apparatus comprising, an infrared light observation unit configured to perform an observation of an eye to be examined by using infrared light, a visible light observation unit configured to perform a visible light observation of the eye to be examined by using visible light, an observation switching unit configured to switch an observation state between the infrared light observation and the visible light observation, a start and completion management unit configured to manage start of an examination and completion of the examination, a photographing unit configured to capture an image of the eye to be examined, and a control unit configured to switch the observation state from the visible light observation to the infrared light observation at least at either one of the start of the examination and the completion of the examination.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 1:
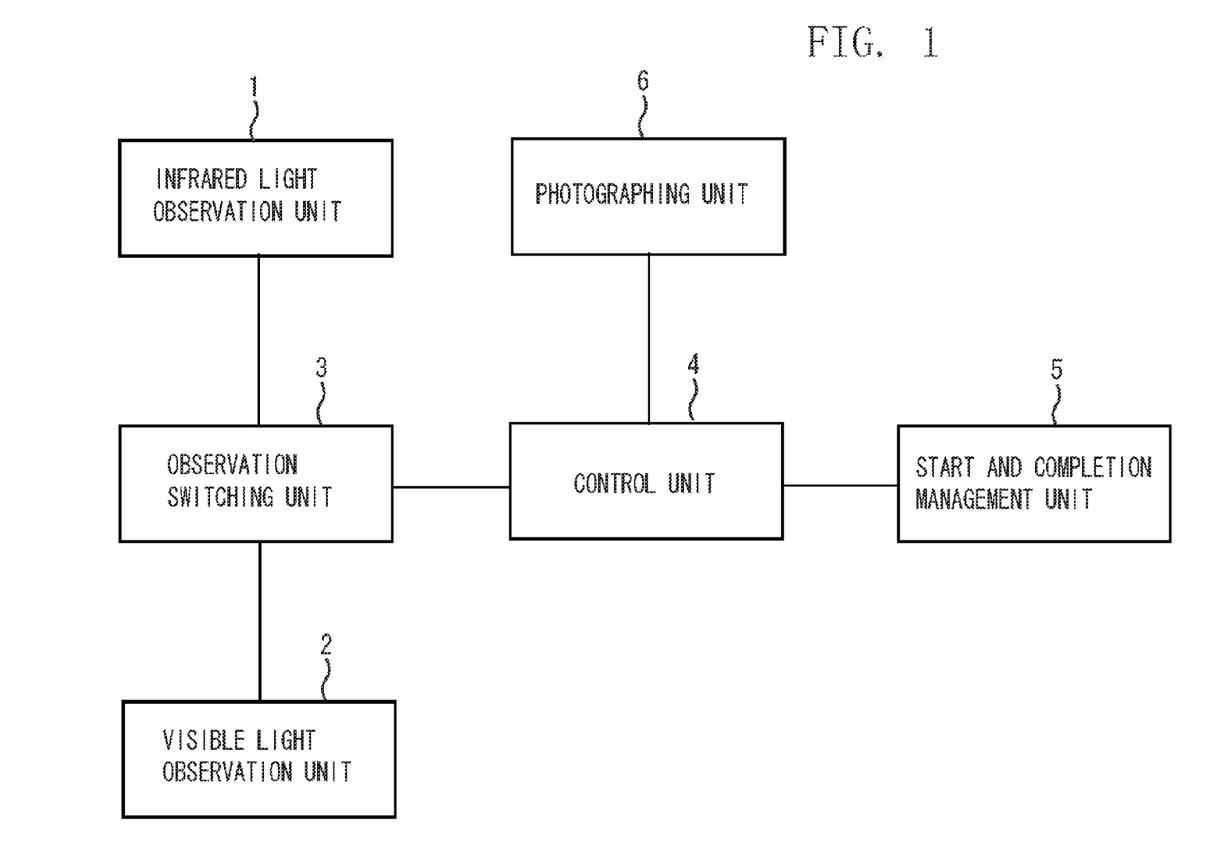
FIG. 1 is a circuit block diagram of an opthalmologic photographing apparatus according to a first exemplary embodiment of the present invention.

FIG. 1 illustrates a circuit block diagram of an opthalmologic photographing apparatus according to a first exemplary embodiment. An infrared light observation unit 1 for observing an eye to be examined with infrared light and a visible light observation unit 2 for observing the eye to be examined with visible light are connected to an observation switching unit 3 that switches between the infrared light observation and the visible light observation. In other words, the observation switching unit may be a physical switch that switches between the infrared light observation unit and the visible light observation unit, or it may be a physical or software-implemented switch that causes either infrared or visible light to be emitted by, for example, a single emitter. The observation switching unit 3 is connected to a control unit 4. A photographing unit 6 that captures an image of the eye to be examined is connected to the control unit 4. A start and completion management unit 5 that manages the start of the examination and the completion of the examination may be connected to the control unit 4, alternatively, this information may be input by an examiner (e.g. an ophthalmologist carrying out the eye exam).

Figure 2:
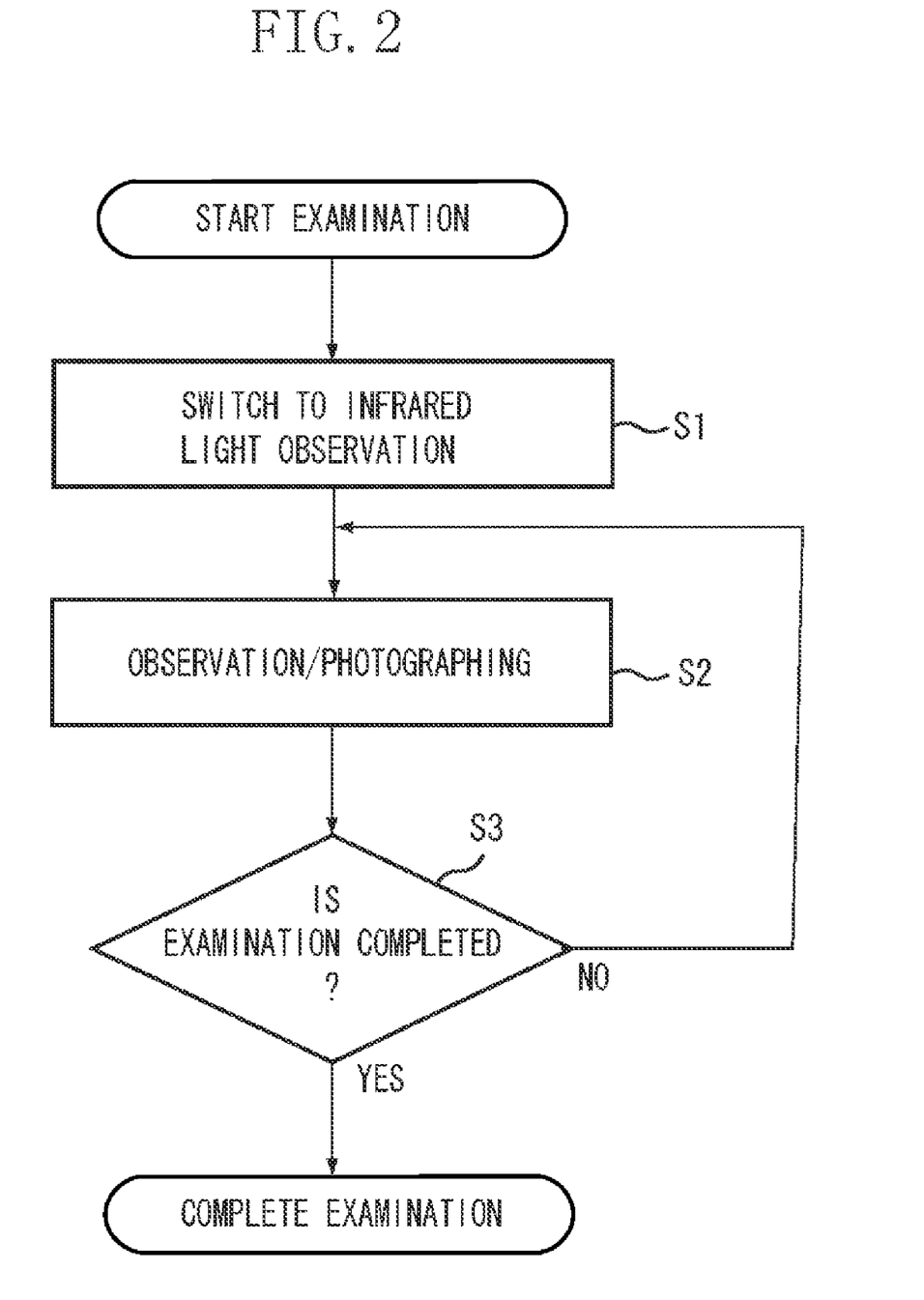
FIG. 2 is a flowchart illustrating an operation of the opthalmologic photographing apparatus according to the first exemplary embodiment of the present invention.

FIG. 2 is a flowchart of a photographing operation using the opthalmologic photographing apparatus according to the present exemplary embodiment.

First, upon detecting a selection of an examination start button (not illustrated), the start and completion management unit 5 starts the examination. In step S1, the control unit 4 selects the infrared light observation unit 1 according to the input from the observation switching unit 3.

Then, in step S2, an examiner performs alignment while observing the eye to be examined, and takes photograph of the eye to be examined by the photographing unit 6. In step S3, the start and completion management unit 5 determines whether the examination is completed according to a selection of an examination complete button (not illustrated), and repeats the process in step S2 until it is determined that the examination is completed. An "examination" of the eye may be considered to include at least one "observation" of the using the photographing unit and either infrared or visible light.

In the first exemplary embodiment, when the examination is started in step S1, although the control unit 4 has switched the observation mode to the infrared light observation, the switching may be executed after it is determined that the examination has been completed in step S3, namely, at the time of completion of the examination.

Figure 3:
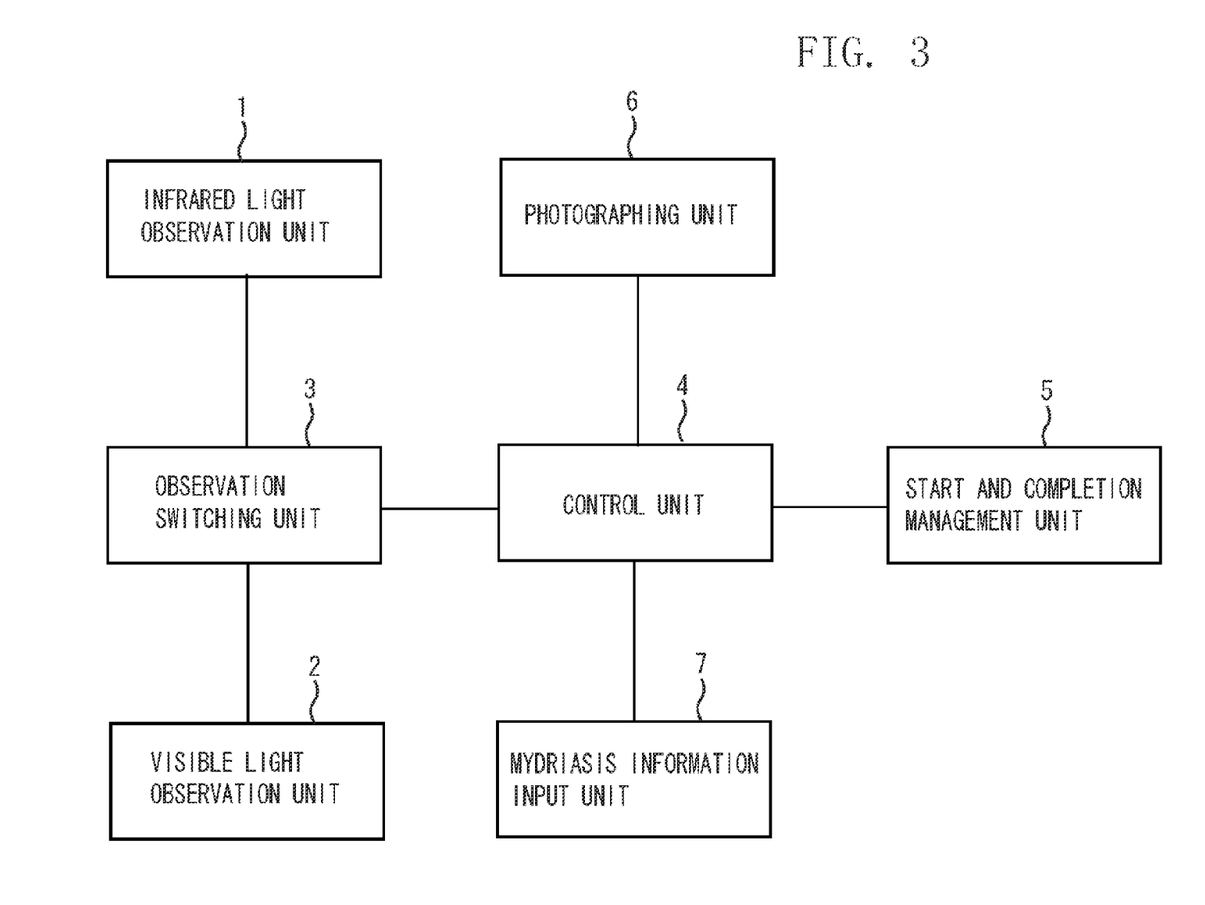
FIG. 3 is a circuit block diagram according to a second exemplary embodiment of the present invention.

FIG. 3 illustrates a circuit block diagram according to a second exemplary embodiment, and components or portions similar to those described in the first exemplary embodiment are denoted by the same reference numerals. In the present second exemplary embodiment, a mydriasis information input unit 7 for inputting information about whether the mydriatic agent is instilled into the eye to be examined, is connected to the control unit 4.

Figure 4:
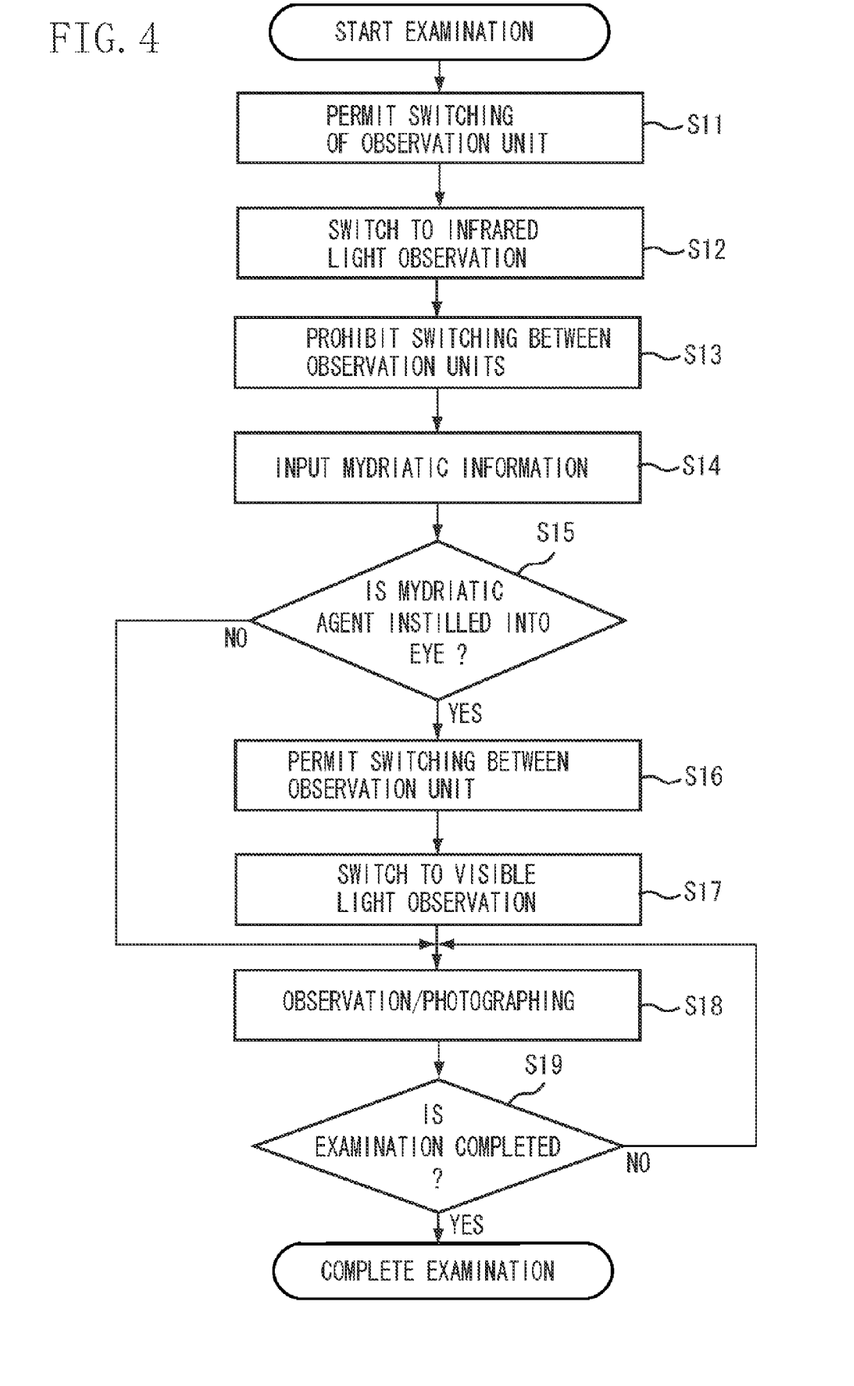
FIG. 4 is a flowchart illustrating an operation of the opthalmologic photographing apparatus according to the second exemplary embodiment of the present invention.

FIG. 4 is a flowchart of a photographing operation according to the present second exemplary embodiment.

First, the start and completion management unit 5 starts examination upon detecting a selection of an examination start button (not illustrated). In step S11, the control unit 4 permits the observation switching unit 3 to switch between the observation units 1 and 2. In step S12, the control unit 4 switches the observation state to the infrared light observation by the infrared light observation unit 1 via the observation switching unit 3.

Figure 5:
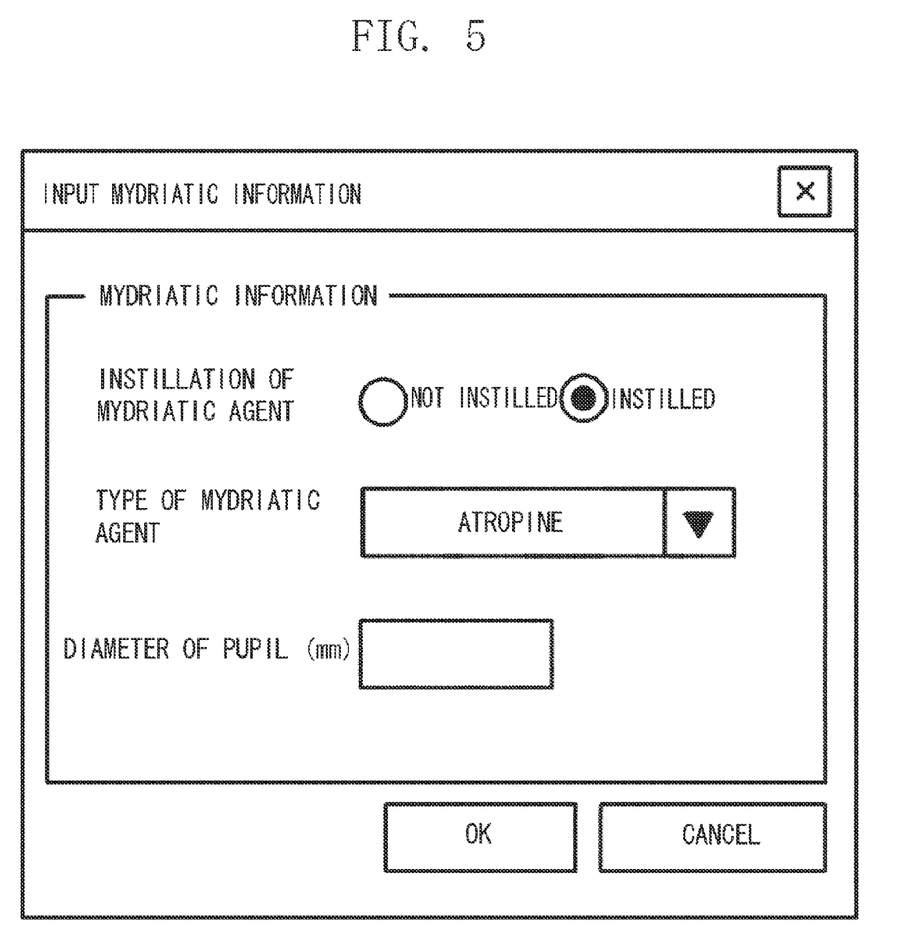
FIG. 5 illustrates an input screen.

Next, in step S13, the control unit 4 prohibits the observation switching unit 3 from switching between the observation units 1 and 2. In step S14, an examiner inputs information about whether the mydriatic agent is instilled into the eye to be examined, for instance, using an input screen 5 of the mydriasis information input unit 7 illustrated in FIG. 5 via the mydriasis information input unit 7. Further, on the input screen 5, the examiner may input additional information such as type of mydriatic agent, diameter of pupil or the like.

Then, in step S15, the control unit 4 determines whether the mydriatic agent is instilled into the eye, which has been input in step S14. If it is determined that the mydriatic agent is instilled into eye (YES in step S15), the processing proceeds to step S16, and the control unit 4 permits switching between the observation units 1 and 2 by the observation switching unit 3.

Next, in step S17, the control unit 4 switches the observation state to the visible light observation by the visible light observation unit 2 via the observation switching unit 3, and subsequently in step S18, the examiner performs alignment while observing the eye to be examined, and takes photograph of the eye to be examined by the photographing unit 6.

Finally, in step S19, the start and completion management unit 5 determines whether the examination is completed, and repeats the process in step S18 until it is determined that the examination is completed (YES in step S19). Further, in step S15, if it is determined that the mydriatic agent is not instilled into eye (NO in step S15), the processing proceeds to step S18, and performs observation and photographing.

In the present second exemplary embodiment, the control unit 4 permits switching between the observation units 1 and 2 of step S11 at the start of the examination, and switches the observation state to the infrared light observation in step S12, and prohibits switching between the observation units 1 and 2 of step S13.

However, the control unit 4 may perform these switching operations and switching prohibition after it is determined that the examination is completed in step S19, namely, at the completion of the examination. Further, the control unit 4 may perform these operations at the both times of the start of the examination and the completion of the examination. Furthermore, in step S17, although the control unit 4 has switched the observation from the infrared light observation to the visible light observation, the observation can be made with infrared light without switching the observation to the visible light observation.

Furthermore, in step S14, although information about whether the mydriatic agent is instilled into the eye is input via the mydriasis information input unit 7 after the start of the examination, it may be input before the start of the examination. In this case, whether the mydriatic agent is instilled into the eye is determined at the start of the examination. If the mydriatic agent is not instilled into the eye, the control unit 4 switches to the infrared light observation at the start of the examination, and prohibits switching between the observation units 1 and 2.

Further, if the mydriatic agent is instilled into the eye, the control unit 4 permits switching to the infrared light observation or the visible light observation, and switching between the observation unit 1 and 2 thereafter, at the start of the examination.

In the present exemplary embodiment, because observation and photographing are performed after the mydriasis information is input, the control unit 4 can control an internal fixation light which presents a fixation target from a photographic optical on-axis, and an external fixation light which presents the fixation target from a photographic optical off-axis as appropriate, in order to guide the eye to be examined in the following manner.

That is, the control unit 4 turns off the internal fixation light, and the external fixation light together at the start of the examination (if the lights are not already turned off). After the input of the mydriasis information, if it is determined that the mydriatic agent has not been instilled into the eye, the control unit 4 turns on the internal fixation light. If it is determined that the mydriatic agent has been instilled into the eye, the control unit 4 turns on the internal fixation light when switching to the infrared light observation, and turns on the external fixation light when switching to the visible light observation.

Figure 6:
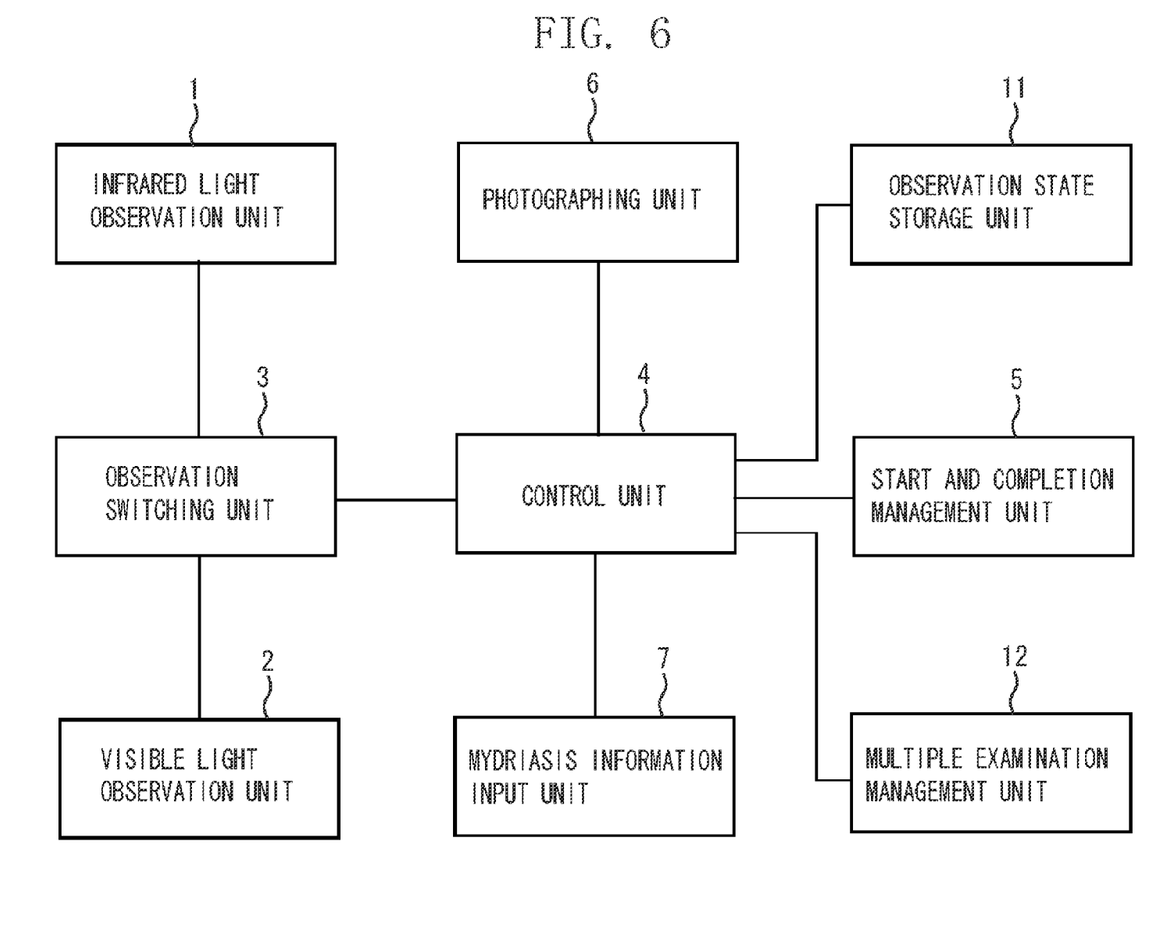
FIG. 6 is a circuit block diagram according to a third exemplary embodiment of the present invention.

FIG. 6 illustrates a circuit block diagram of an opthalmologic photographing apparatus according to a third exemplary embodiment. In the present exemplary embodiment, an observation state storage unit 11 that stores observation state for each examination and multiple examination management units 12 that manages switching between examinations are connected to the control unit 4 for allowing a plurality of examinations to be implemented in parallel. Features in FIG. 6 of the third embodiment that may be the same as features of the first and second embodiments illustrated in FIGS. 1 and 3 are denoted with the same reference numerals.

Figure 7:
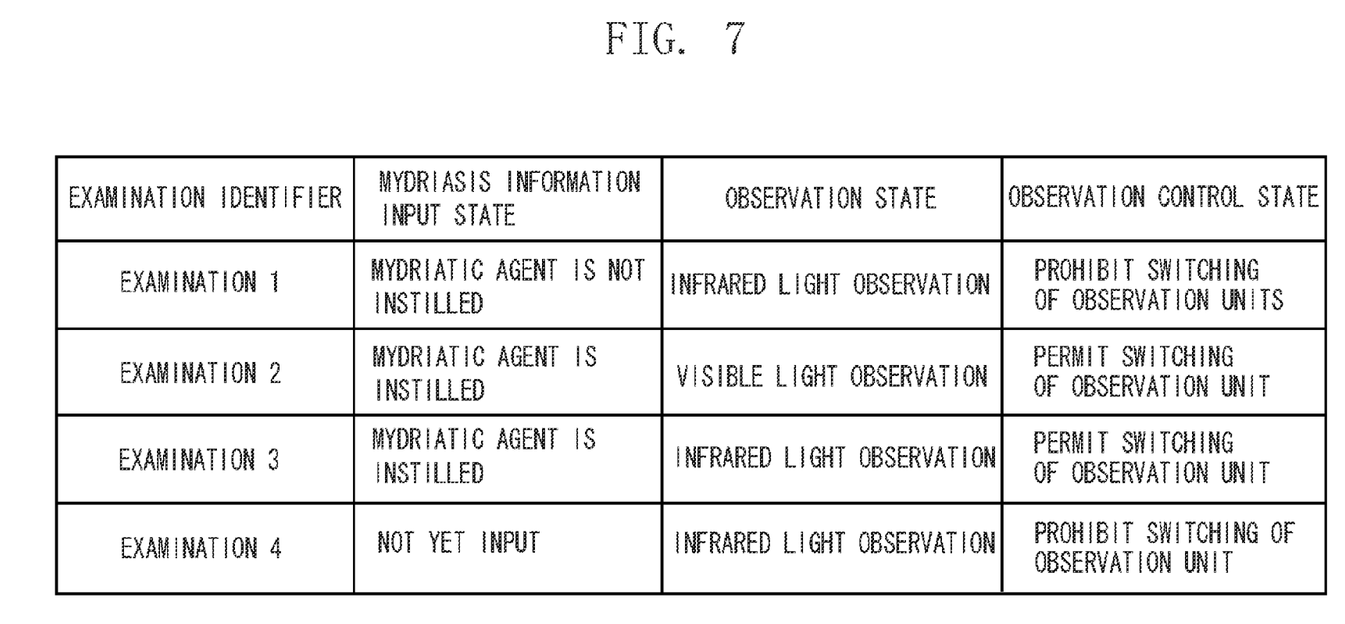
FIG. 7 is an example of a list of observation states.

FIG. 7 illustrates an example of a list of observation states, which is stored in the observation state storage unit 11. The observation state storage unit 11 stores "examination identifier", "mydriasis information input state", "observation unit", and "observation control state" for all examinations to be implemented, as observation states.

In the "mydriasis information input state", the observation state storage unit 11 stores input states such as "not yet input", "mydriatic agent is not instilled", "mydriatic agent is instilled" by the mydriasis information input unit 7. The observation state storage unit 11 stores whether the "observation state" is in a state of the infrared light observation or the visible light observation, and whether the "observation control state" is in a state of switching permission between the observation units 1 and 2, or switching prohibition between the observation units 1 and 2.

Figure 8:
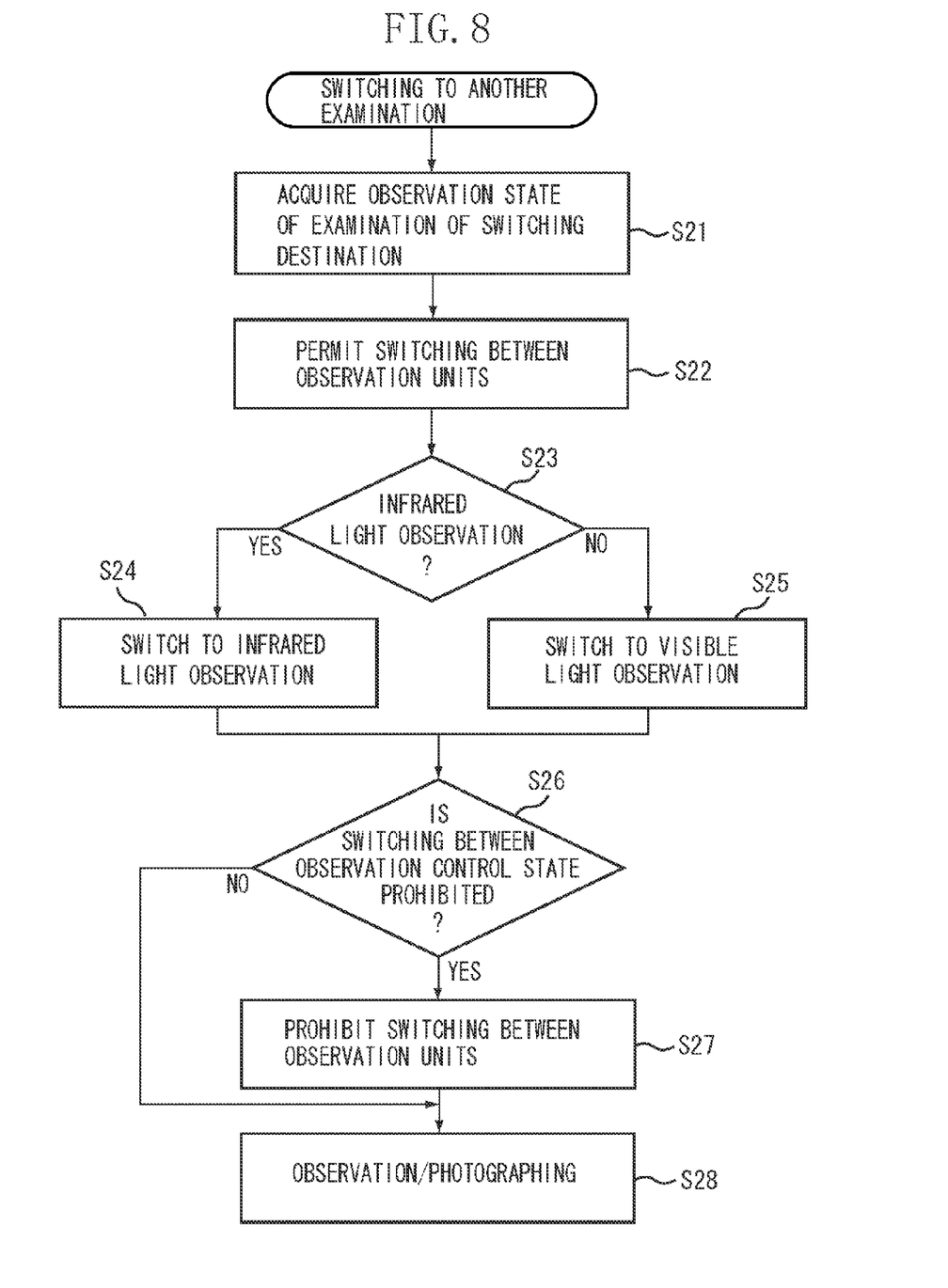
FIG. 8 is a flowchart illustrating an operation of the opthalmologic photographing apparatus according to the third exemplary embodiment of the present invention.

FIG. 8 is a flowchart of a photographing operation in the present exemplary embodiment.

When the multiple examination management unit 12 detects switching to another examination, in step S21, the control unit 4 acquires an observation state of the "examination identifier" of switching destination (another eye being examined), from the observation state storage unit 11.

Next in step S22, the control unit 4 permits switching between the observation units 1 and 2 by the observation switching unit 3. In step S23, the control unit 4 determines whether the observation state is an infrared light observation. If it is determined as the infrared light observation (YES in step S23), the processing proceeds to step S24. In step S24, the control unit 4 switches the observation state to the infrared light observation by the observation switching unit 3, and then the processing proceeds to step S26. Alternatively, in step S23, if it is determined that the visible light observation is performed (NO in step S23), the processing proceeds to step S25. In step S25, the control unit 4 switches the observation state to the visible light observation by the observation switching unit 3, and the processing proceeds to step S26.

Then, in step S26, the control unit 4 determines the "observation control state". If the "observation control state" is switching prohibition between the observation units 1 and 2, the processing proceeds to step S27. In step S27, the control unit 4 prohibits switching between the observation units 1 and 2 by the observation switching unit 3. In step S28, an examiner performs alignment while observing the eye to be examined, and photographs the eye to be examined by the photographing unit 6.

In step S26, if the "observation control state" is a switching permission between the observation units 1 and 2, the processing proceeds to step S28.

In the present exemplary embodiment, although the "mydriasis information input state" is stored in order to illustrate an example of the "observation state", and the "observation control state" according to the mydriasis information input state, the "mydriasis information input state" may not need to be stored.

Although the present exemplary embodiment includes the mydriasis information input unit 7, and the control of switching permission, and prohibition between the "observation units" is performed is described, the controls of switching permission, and prohibition between the observation units 1 and 2 may not need to be performed in similar manner to the first exemplary embodiment. In this case, steps S22, S26, and S27 in the flowchart of FIG. 8 are unnecessary, and the "observation control state" illustrated in FIG. 7 may not need to be stored.

Figure 9:
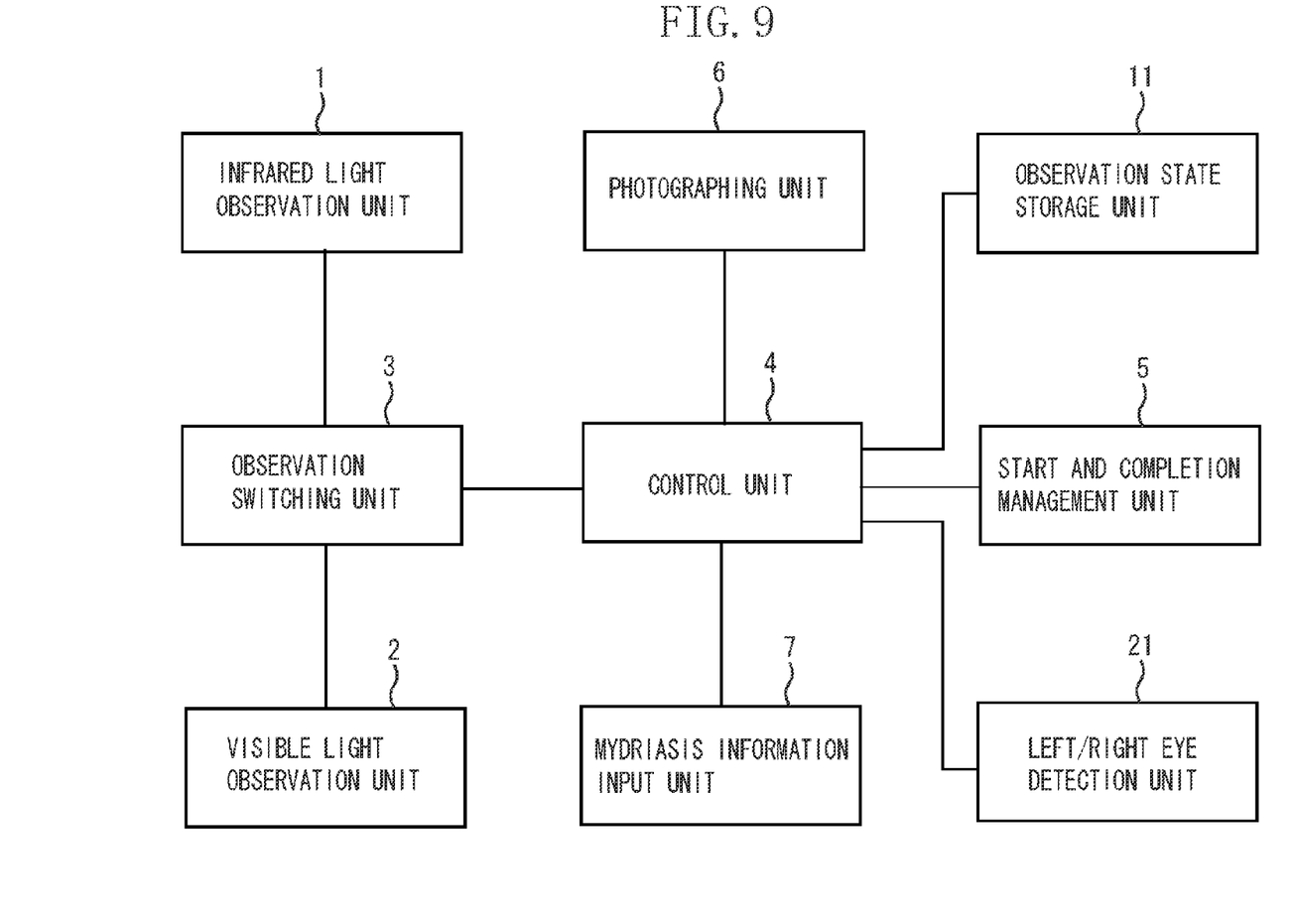
FIG. 9 is a circuit block diagram according to a fourth exemplary embodiment of the present invention.

FIG. 9 is a circuit block diagram according to a fourth exemplary embodiment. In the present fourth exemplary embodiment, a left/right eye detection unit 21 is provided for detecting whether the eye to be examined is the left eye or the right eye, in place of the multiple examination management unit 12 according to the third exemplary embodiment. The rest of the reference numerals of FIG. 9 are the same as in FIG. 6 illustrating the third embodiment.

Figure 10:
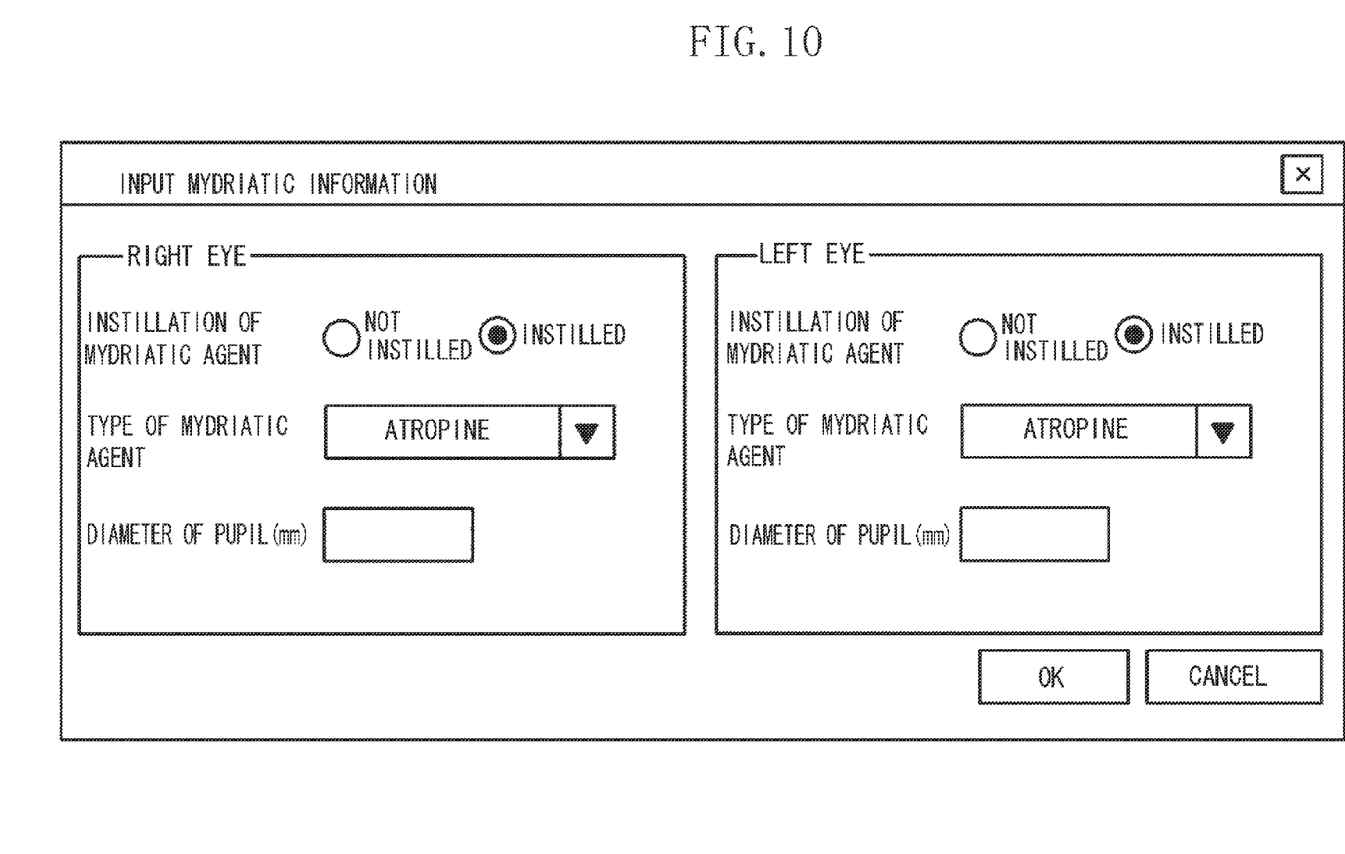
FIG. 10 illustrates an input screen.
Figure 11:
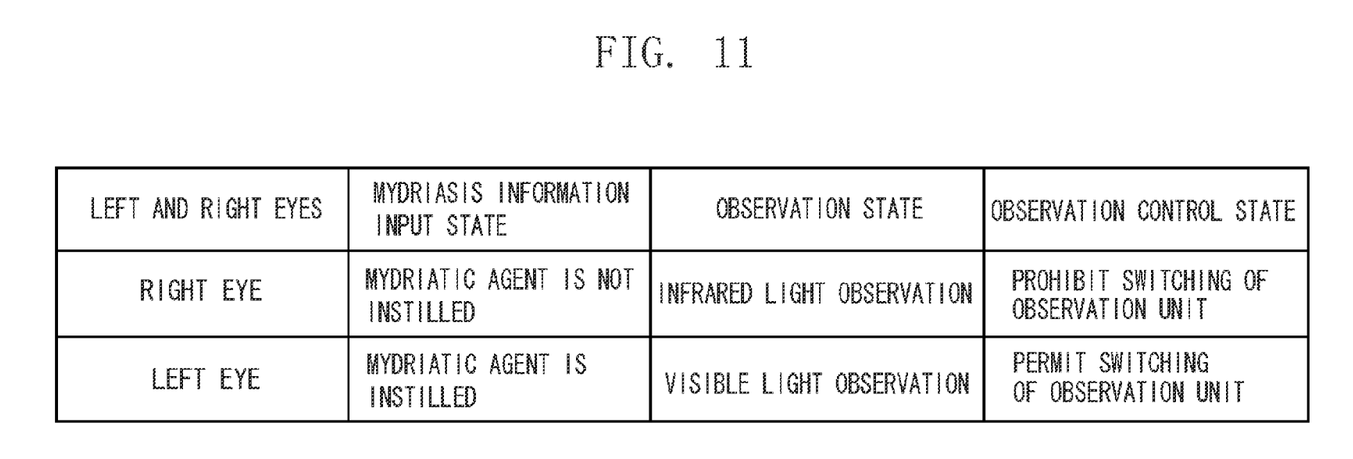
FIG. 11 is an example of a list of observation states.

FIG. 10 illustrates an input screen of the mydriasis information input unit 7 that can input whether the mydriatic agent is instilled for each of the left and right eyes. FIG. 11 illustrates an example of a list of observation states to be stored in the observation state storage unit 11, and the observation state storage unit 11 stores, "left or right eye", "mydriasis information input state", "observation state", and "observation control state" as the observation states, for one examination under implementation.

Input states ("not yet input", "mydriatic agent is not instilled", "mydriatic agent is instilled") obtained by the mydriasis information input unit 7 are stored in the "mydriasis information input state", and whether the infrared light observation or the visible light observation is used is stored in the "observation state". Which of the switching permission of the observation units 1 and 2, and the switching prohibition of the observation units 1 and 2 is selected, is stored in the "observation control state".

Figure 12:
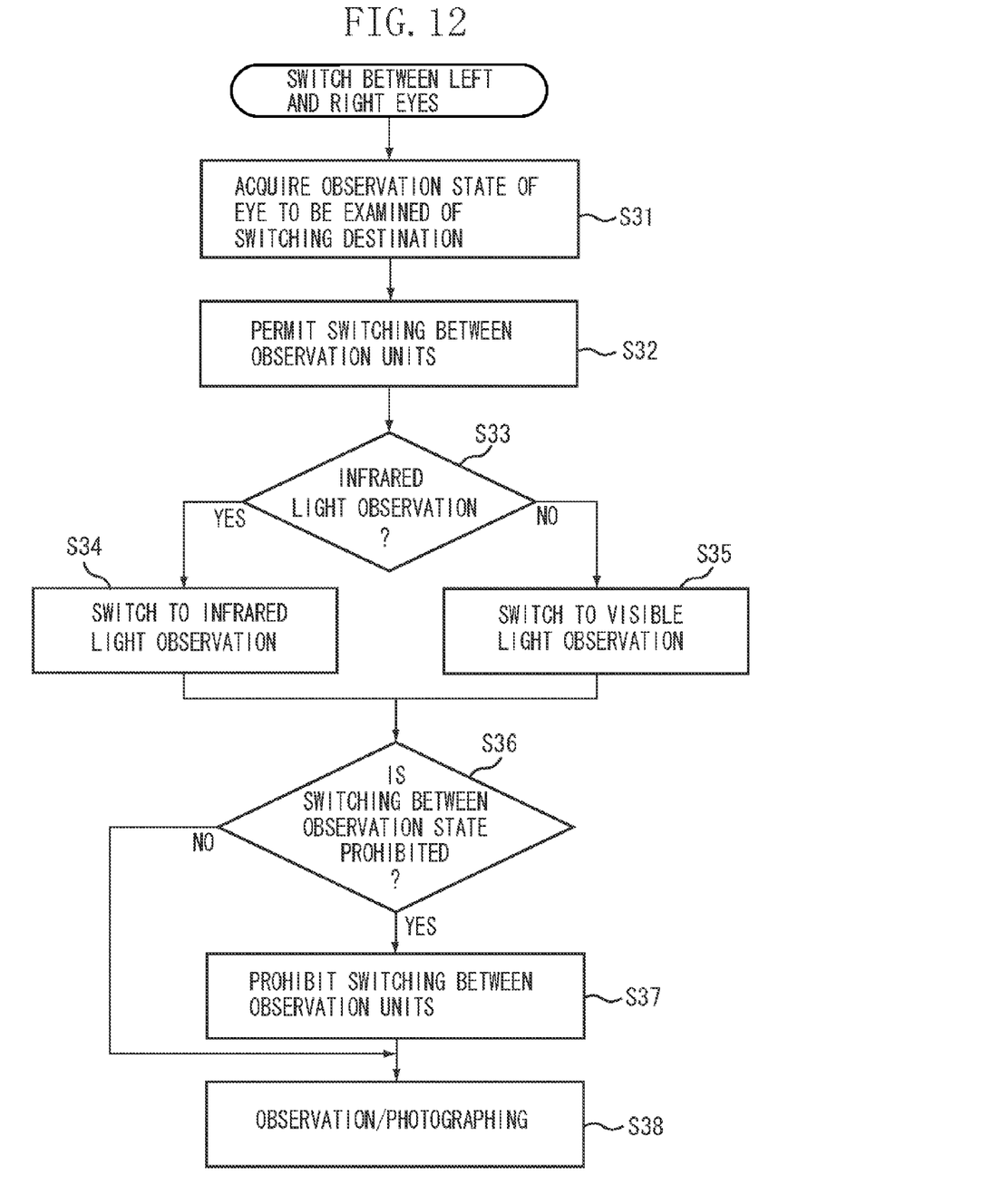
FIG. 12 is a flowchart illustrating an operation of the opthalmologic photographing apparatus according to the fourth exemplary embodiment of the present invention.

FIG. 12 is a flowchart of a photographing operation in the present exemplary embodiment.

When the left/right eye detection unit 21 detects switching between left and right eyes, then in step S31, the control unit 4 acquires observation state of the eye of the switching destination from the observation state storage unit 11. In step S32, the control unit 4 permits switching between the observation units 1 and 2 by the observation switching unit 3.

Then, in step S33, the control unit 4 determines whether the acquired "observation state" is an infrared light observation. If the acquired "observation state" is the infrared light observation (YES in step S33), the processing proceeds to step S34. In step S34, the control unit 4 switches the "observation state" to the infrared light observation by the observation switching unit 3, and the processing proceeds to step S36.

Further, in step S33, if the "observation state" is a visible light observation (NO in step S33), the processing proceeds to step S35. In step S35, the control unit 4 switches the observation state to the visible light observation by the observation switching unit 3, and the processing proceeds to step S36.

Then, in step S36, the control unit 4 determines the "observation control state" acquired in steps S34 and S35. If the "observation control state" is the switching prohibition between the observation units 1 and 2 (YES in step S36), the processing proceeds to step S37. In step S37, the control unit 4 prohibits switching between the observation units 1 and 2 by the observation switching unit 3, and then in step S38, an examiner performs alignment while observing the eye to be examined, and photographs the eye to be examined by the photographing unit 6. In step S36, if the "observation control state" is the switching permission between the observation units 1 and 2 (NO in step S36), the processing proceeds to step S38.

In the present exemplary embodiment, although the "mydriasis information input state" is stored in order to illustrate an example of the "observation state", and the "observation control state" according to the mydriasis information input state, the "mydriasis information input state" may not need to be stored.

Further, the case including the mydriasis information input unit 7, and performing control of switching permission and prohibition of the observation units 1 and 2 is described above. However, the control of the switching permission and prohibition of the observation units 1 and 2 may not need to be performed in similar manner to the exemplary embodiment 1.

In this case, in the flowchart of FIG. 12, steps S32, S36, and S37 are unnecessary, and the "observation control state" of FIG. 11 may not need to bee stored.

Furthermore, in the present exemplary embodiment, although the case where an examination is under implementation is described, the examination can be combined with the case of a plurality of examinations of the third exemplary embodiment.

According to an opthalmologic photographing apparatus of the exemplary embodiments of the present invention, the control unit 4 automatically switches the observation state to the infrared light observation, at least at either one of the start of the examination or the completion of the examination. As a result, if the infrared light observation is performed without the mydriatic agent being instilled into the eye to be examined, the miosis of the eye, which may occur due to a switching mistake between the observation units, can be prevented.

Further, at least at either one of the start of the examination or the completion of the examination, the control unit 4 automatically switches the observation state to the infrared light observation as well as prohibits switching between the observation units, and permits switching between the observation units when the information is input that the mydriatic agent is instilled through the mydriasis information input. For this reason, if the infrared light observation is performed without the mydriatic agent being instilled into the eye, the miosis of the eye to be examined by operational mistake can be prevented.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2008-269957 filed Oct. 20, 2008, which is hereby incorporated by reference herein in its entirety.

What is claimed is:

1. An ophthalmologic photographing apparatus comprising:
   illumination optical system configured to illuminate an eye to be examined with visible light or infrared light;
   switching means configured to switch between the visible light and the infrared light;
   mode selection means configured to select a mydriatic mode in which the eye to be examined is illuminated with the visible light or a non-mydriatic mode in which the eye to be examined is illuminated with the infrared light;
   control means configured to control the switching means to switch the visible light to the infrared light if the eye to be examined is photographed in the mydriatic mode.

2. The ophthalmologic photographing apparatus according to claim 1, wherein the infrared light is maintained if the non-mydriatic mode is selected after the switching means switches the visible light to infrared light.

3. The ophthalmologic photographing apparatus according to claim 1, wherein the mode selection means includes mydriasis information input means configured to input information indicating whether a mydriatic agent is instilled into the eye to be examined or not.

4. The ophthalmologic photographing apparatus according to claim 3 further comprising:
   an internal fixation light configured to show a fixation target from a photographic optical on-axis so as to guide the eye to be examined; and
   an external fixation light configured to show the fixation target from a photographic optical off-axis so as to guide the eye to be examined,
   wherein the internal fixation light is turned on if the mydriasis information input means input information indicating that the mydriatic agent is not instilled into the eye to be examined, and the external fixation light is turned on if the mydriasis information input means input information indicating that the mydriatic agent is instilled into the eye to be examined.

5. The ophthalmologic photographing apparatus according to claim 3 further comprising:
   left or right eye detection means configured to detect whether the eye to be examined is a left eye or right eye; and
   observation state storage means configured to store information indicating at least whether the observation state is the infrared light or the visible light for each of the left and right eyes,
   wherein the mydriasis information input means includes information indicating whether the mydriatic agent is instilled into the eye to be examined or not for each of the left and right eyes, and
   wherein, when the left or right eye detection means detects switching between left and right eyes, the observation state is switched to a state for observing the switched eye stored in the observation state storage means.

6. The ophthalmologic photographing apparatus according to claim 1 further comprising:
   photographing means configured to capture an image of the eye to be examined with photographing light, wherein the illumination optical system includes infrared light observation means configured to illuminate the eye to be examined with the infrared light and visible light observation means configured to illuminate the eye to be examined with the visible light.

7. The ophthalmologic photographing apparatus according to claim 1 further comprising:

photographing means configured to capture an image of the eye to be examined with photographing light, wherein the illumination optical system includes a light source, wavelength selection means configured to select the visible light or the infrared light among light from the light source, and irradiation means configured to irradiate the eye to be examined with the light of wavelength selected by the wavelength selection means.

8. The ophthalmologic photographing apparatus according to claim 1, wherein the illumination optical system includes photographing means configured to capture an image of the eye to be examined with photographing light.

9. The ophthalmologic photographing method according to claim 1, further comprising an internal fixation light configured to show a fixation target from a photographic optical on-axis so as to guide the eye to be examined; and wherein the control means controls the switching means to switch the visible light to the infrared light and controls the internal fixation light to turn on if the eye to be examined is photographed in the mydriatic mode.

10. The ophthalmologic photographing method according to claim 1, wherein the control means controls the switching means to switch the infrared light to the visible light if the mydriatic mode is selected after the switching means switches the visible light to the infrared light.

11. The ophthalmologic photographing method according to claim 1, further comprising an external fixation light configured to show the fixation target from a photographic optical off-axis so as to guide the eye to be examined, and wherein the control means controls the switching means to switch the infrared light to the visible light and controls the external fixation light to turn on if the mydriatic mode is selected after the switching means switches the visible light to the infrared light.

12. An ophthalmologic photographing apparatus comprising:

illumination optical system configured to illuminate an eye to be examined with visible light or infrared light;

an internal fixation light configured to show a fixation target from a photographic optical on-axis so as to guide the eye to be examined;

switching means configured to switch the visible light or the infrared light; and control means configured to control the switching means to switch the visible light to the infrared light, and the internal fixation light is turned on if the eye to be examined is photographed in a mydriatic mode.

13. An ophthalmologic photographing apparatus comprising:

illumination optical system configured to illuminate an eye to be examined with visible light or infrared light;

switching means configured to switch an observation state between visible light illumination of an eye to be examined and infrared light illumination of the eye to be examined; and control means configured to control the switching means to switch the observation state from the visible light to the infrared light if the eye to be examined is photographed in a mydriatic mode.

14. An ophthalmologic photographing method comprising:

an illumination step of illuminating an eye to be examined with visible light;

a photographing step of capturing an image of the eye to be examined in a mydriatic mode;

a first switching step of switching illumination light from the visible light to the infrared light after the illumination step and the photographing step; and a second switching step of switching the illumination light from the infrared light to the visible light when the mydriatic mode is selected after the first switching step.

15. The ophthalmologic photographing method according to claim 14, wherein the infrared light is maintained as the illumination light when a non-mydriatic mode is selected after the first switching step.

16. The ophthalmologic photographing method according to claim 14, wherein, the mode is selected by inputting mydriasis information indicating whether a mydriatic agent is instilled into the eye to be examined or not.

* * * * *